United States Patent [19]

Catterall et al.

[11] Patent Number: 5,623,051

[45] Date of Patent: Apr. 22, 1997

[54] METHODS AND COMPOSITIONS FOR SCREENING FOR PRESYNAPTIC CALCIUM CHANNEL BLOCKERS

[75] Inventors: William A. Catterall; Zu-Hang Sheng, both of Seattle, Wash.

[73] Assignee: University of Washington, Seattle, Wash.

[21] Appl. No.: 337,602

[22] Filed: Nov. 10, 1994

[51] Int. Cl.$^6$ .................... C07K 14/47; C07K 14/705; G01N 33/566

[52] U.S. Cl. .................... 530/324; 436/501; 530/350

[58] Field of Search .................... 436/501, 503; 514/8, 12, 21; 530/322, 324, 350, 395, 839

[56] References Cited

FOREIGN PATENT DOCUMENTS 04083  3/1993  WIPO .

OTHER PUBLICATIONS

Science, vol. 257, Issued 10 Jul. 1992, Bennett et al, "Syntaxin: A Synaptic Protein Implicated in Docking . . . ", pp. 255–259.

Cell, vol. 74, Issued 10 Sep. 1993, Bennett et al, "The Syntaxin Family of Vesicular Transport Receptors", pp. 863–873.

J. Biol. Chem., vol. 269, No. 9, Issued 04 Mar. 1994, Leveque et al, "Purification of the N–type Calcium Channel . . . ", pp. 6306–6312.

Primary Examiner—Jeffrey E. Russel
Attorney, Agent, or Firm—Seed and Berry LLP

[57] ABSTRACT

Methods and compositions related to the identification of compounds that block neurotransmitter release are disclosed. Using the methods of the present invention, candidate compounds may be screened for the ability to bind to presynaptic calcium channels such that the docking of presynaptic vesicles to presynaptic calcium channels will be inhibited. The present invention also discloses peptides useful in the screening methods.

16 Claims, 13 Drawing Sheets

Fig.11A-710 Val Asp Asn Leu Ala Asn Ala Gln Glu Leu Thr Lys Asp Glu Glu Glu Met Glu Glu Ala Ala Asn Gln Lys Leu 734
Fig.11B-710 . Asp Asn Leu Ala Asn Ala Gln Glu Leu Thr Lys Asp Glu Glu Glu Met Glu Glu Ala Ala Asn Gln Lys Leu 733

735 Ala Leu Gln Lys Ala Lys Glu Val Ala Glu Val Ser Pro Met Ser Ala Ala Asn Ile Ser Ile Ala Ala Arg Gln 759
734 Ala Leu Gln Lys Ala Lys Glu Val Ala Glu Val Ser Pro Met Ser Ala Ala Asn Ile Ser Ile Ala Ala Arg Gln 758

760 Gln Asn Ser Ala Lys Ala Arg Ser Val Trp Glu Gln Arg Ala Ser Gln Leu Arg Leu Gln Asn Leu Arg Ala Ser 784
759 Gln Asn Ser Ala Lys Ala Arg Ser Val Trp Glu Gln Arg Ala Ser Gln Leu Arg Leu Gln Asn Leu Arg Ala Ser 783

785 Cys Glu Ala Leu Tyr Ser Glu Met Asp Pro Glu Glu Arg Leu Arg Tyr Ala Ser Thr Arg His Val Arg Pro Asp 809
784 Cys Glu Ala Leu Tyr Ser Glu Met Asp Pro Glu Glu Arg Leu Arg Phe Ala Thr Thr Arg His Leu Arg Pro Asp 808

810 Met Lys Thr His Met Asp Arg Pro Leu Val Val Glu Pro Gly Arg Asp Gly Leu Arg Gly Pro Ala Gly Asn Lys 834
809 Met Lys Thr His Leu Asp Arg Pro Leu Val Val Glu Leu Gly Arg Asp Gly Ala Arg Gly Pro Val Gly Gly Lys 833

835 Ser Lys Pro Glu Gly Thr Glu Ala Thr Glu Gly Ala Asp Pro Pro Arg Arg His His Arg His Arg Asp Arg Asp 859
834 Ala Arg Pro Glu Ala Ala Glu Ala Pro Glu Gly Val Asp Pro Pro Arg Arg His His Arg His Arg Asp Lys Asp 858

860 Lys Thr Ser Ala Ser Thr Pro Ala Gly Gly Glu Gln Asp Arg Thr Asp Cys Pro Lys Ala Glu Ser Thr Glu Thr 884
859 Lys . . . . Thr Pro Ala Ala Gly Asp Gln Asp Arg Ala Glu Ala Pro Lys Ala Glu Ser Gly Glu Pro 879

885 Gly Ala Arg Glu Glu Arg Ala Arg Pro Arg Arg Ser His Ser Lys Glu Ala Pro Gly Ala Asp Thr Gln Val Arg 909
880 Gly Ala Arg Glu Glu Arg Pro Arg Pro His Arg Ser His Ser Lys Glu Ala Ala Gly Pro . Pro Glu Ala Arg 903

910 Cys Glu Arg . . . . . . . . Ser Arg Arg His His Arg Arg Gly Ser Pro Glu Glu Ala Thr 926
904 Ser Glu Arg Gly Arg Gly Pro Gly Pro Glu Gly Gly Arg Arg His His Arg Arg Gly Ser Pro Glu Glu Ala Ala 928

927 Glu Arg Glu Pro Arg Arg His Arg Ala His Arg His Ala Gln Asp Ser Ser Lys Glu Gly Lys Glu Gly Thr Ala 951
929 Glu Arg Glu Pro Arg Arg His Arg Ala His Arg His . Gln Asp Pro Ser Lys Glu Cys Ala Gly Ala . . 950

952 Pro Val Leu Val Pro Lys Gly Glu Arg Arg Ala Arg His Arg . Gly Pro Arg Thr Gly Pro Arg Glu Thr Glu 975
951 . . . . . Lys Gly Glu Arg Arg Ala Arg His Arg Gly Gly Pro Arg Ala Gly Pro Arg Glu Ala Glu 970

976 Asn Ser Glu Glu Pro Thr Arg Arg His Arg Ala Lys His Lys Val Pro Pro Thr Leu Glu Pro . . . . 996
971 Ser Gly Glu Glu Pro Ala Arg Arg His Arg Ala Arg His Lys Ala Gln Pro Ala His Glu Ala Val Glu Lys Glu 995

997 . Pro Glu Arg Glu Val Ala Glu Lys Glu Ser Asn Val Val Glu Gly Asp Lys Glu Thr . . Arg Asn His 1018
996 Thr Thr Glu Lys Glu Ala Thr Glu Lys Glu Ala Glu Ile Val Glu Ala Asp Lys Glu Lys Glu Leu Arg Asn His 1020

1019 Gln Pro Lys Glu Pro Arg Cys Asp Leu Glu Ala Ile Ala Val Thr Gly Val Gly Ser Leu His Met Leu Pro Ser 1043
1021 Gln Pro Arg Glu Pro His Cys Asp Leu Glu Thr Ser Gly Thr Val Thr Val Gly Pro Met His Thr Leu Pro Ser 1045

1044 Thr Cys Leu Gln Lys Val Asp Glu Gln Pro Glu Asp Ala Asp Asn Gln Arg Asn Val Thr Arg Met Gly Ser Gln 1068
1046 Thr Cys Leu Gln Lys Val Glu Glu Gln Pro Glu Asp Ala Asp Asn Gln Arg Asn Val Thr Arg Met Gly Ser Gln 1070

1069 Pro Ser Asp Pro Ser Thr Thr Val His Val Pro Val Thr Leu Thr Gly Pro Pro Gly Glu Ala Thr Val Val Pro 1093
1071 Pro Pro Asp Pro Asn Thr Ile Val His Ile Pro Val Met Leu Thr Gly Pro Leu Gly Glu Ala Thr Val Val Pro 1095

1094 Ser Ala Asn Thr Asp Leu Glu Gly Gln Ala Glu Gly Lys Lys Glu Ala Glu Ala Asp Asp Val Leu Arg Arg Gly 1118
1096 Ser Gly Asn Val Asp Leu Glu Ser Gln Ala Glu Gly Lys Lys Glu Val Glu Ala Asp Asp Val Met Arg Ser Gly 1120

1119 Pro Arg Pro Ile Val Pro Tyr Ser Ser Met Phe Cys Leu Ser Pro Thr Asn Leu Leu Arg Arg Phe Cys His Tyr 1143
1121 Pro Arg Pro Ile Val Pro Tyr Ser Ser Met Phe Cys Leu Ser Pro Thr Asn Leu Leu Arg Arg Phe Cys . . 1143

```
  1  Met Lys Asp Arg Thr Gln Glu Leu Arg Thr Ala Lys Asp Ser Asp Asp Asp Val Thr Val Asp
 26  Arg Asp Arg Phe Met Asp Glu Phe Phe Glu Gln Val Glu Glu Ile Arg Gly Phe Ile Asp Lys Ile Ala Glu Asn
 51  Val Glu Glu Val Lys Arg Lys His Ser Ala Ile Leu Ala Ser Pro Asn Pro Asp Glu Lys Thr Lys Glu Glu Leu
 76  Glu Glu Leu Met Ser Asp Ile Lys Lys Thr Ala Asn Lys Val Arg Ser Lys Leu Lys Ser Ile Glu Gln Ser Ile
101  Glu Gln Glu Glu Gly Leu Asn Arg Ser Ser Ala Asp Leu Arg Ile Arg Lys Thr Gln His Ser Thr Leu Ser Arg
126  Lys Phe Val Glu Val Met Ser Glu Tyr Asn Ala Thr Gln Ser Asp Tyr Arg Glu Arg Cys Lys Gly Arg Ile Gln
151  Arg Gln Leu Glu Ile Thr Gly Arg Thr Thr Thr Ser Glu Glu Leu Glu Asp Met Leu Glu Ser Gly Asn Pro Ala
176  Ile Phe Ala Ser Gly Ile Ile Met Asp Ser Ser Ile Ser Lys Gln Ala Leu Ser Glu Ile Glu Thr Arg His Ser
201  Glu Ile Ile Lys Leu Glu Asn Ser Ile Arg Glu Leu His Asp Met Phe Met Asp Met Ala Met Leu Val Glu Ser
226  Gln Gly Glu Met Ile Asp Arg Ile Glu Tyr Asn Val Glu His Ala Val Asp Tyr Val Glu Arg Ala Val Ser Asp
251  Thr Lys Lys Ala Val Lys Tyr Gln Ser Lys Ala Arg Arg Lys Lys Ile Met Ile Ile Cys Cys Val Ile Leu
276  Gly Ile Ile Ala Ser Thr Ile Gly Gly Ile Phe Gly
```

*Figure 12*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 87 amino acids
( B ) TYPE: amino acid
( C ) STRANDEDNESS:
( D ) TOPOLOGY: linear ( x i ) SEQUENCE DESCRIPTION: SEQ ID NO:1:

```
Ala  Ser  Gln  Leu  Arg  Leu  Gln  Asn  Leu  Arg  Ala  Ser  Cys  Glu  Ala  Leu
1                   5                        10                      15

Tyr  Ser  Glu  Met  Asp  Pro  Glu  Glu  Arg  Leu  Arg  Tyr  Ala  Ser  Thr  Arg
              20                       25                           30

Asn  Val  Arg  Pro  Asp  Met  Lys  Thr  His  Met  Asp  Arg  Pro  Arg  Val  Val
          35                      40                      45

Glu  Pro  Gly  Arg  Asp  Gly  Leu  Arg  Gly  Pro  Ala  Gly  Asn  Lys  Ser  Lys
     50                      55                       60

Pro  Glu  Gly  Thr  Glu  Ala  Thr  Glu  Gly  Ala  Asp  Pro  Pro  Arg  Arg  His
65                            70                  75                       80

His  Arg  His  Arg  Asp  Arg  Asp
                    85
```

( 2 ) INFORMATION FOR SEQ ID NO:2:

( i ) SEQUENCE CHARACTERISTICS:
( A ) LENGTH: 434 amino acids
( B ) TYPE: amino acid
( C ) STRANDEDNESS:
( D ) TOPOLOGY: linear ( x i ) SEQUENCE DESCRIPTION: SEQ ID NO:2:

```
Val  Asp  Asn  Leu  Ala  Asn  Ala  Gln  Glu  Leu  Thr  Lys  Asp  Glu  Glu  Glu
1                   5                        10                      15

Met  Glu  Glu  Ala  Ala  Asn  Gln  Lys  Leu  Ala  Leu  Gln  Lys  Ala  Lys  Glu
              20                       25                           30

Val  Ala  Glu  Val  Ser  Pro  Met  Ser  Ala  Ala  Asn  Ile  Ser  Ile  Ala  Ala
          35                      40                      45
```

```
Arg Gln Gln Asn Ser Ala Lys Ala Arg Ser Val Trp Glu Gln Arg Ala
         50                  55                  60
Ser Gln Leu Arg Leu Gln Asn Leu Arg Ala Ser Cys Glu Ala Leu Tyr
 65              70                  75                      80
Ser Glu Met Asp Pro Glu Glu Arg Leu Arg Tyr Ala Ser Thr Arg His
                 85                  90                  95
Val Arg Pro Asp Met Lys Thr His Met Asp Arg Pro Leu Val Val Glu
             100             105             110
Pro Gly Arg Asp Gly Leu Arg Gly Pro Ala Gly Asn Lys Ser Lys Pro
         115             120             125
Glu Gly Thr Glu Ala Thr Glu Gly Ala Asp Pro Pro Arg Arg His His
     130             135             140
Arg His Arg Asp Arg Asp Lys Thr Ser Ala Ser Thr Pro Ala Gly Gly
145             150             155                         160
Glu Gln Asp Arg Thr Asp Cys Pro Lys Ala Glu Ser Thr Glu Thr Gly
                 165             170             175
Ala Arg Glu Glu Arg Ala Arg Pro Arg Ser His Ser Lys Glu Ala
             180             185             190
Pro Gly Ala Asp Thr Gln Val Arg Cys Glu Arg Ser Arg Arg His His
         195             200             205
Arg Arg Gly Ser Pro Glu Glu Ala Thr Glu Arg Glu Pro Arg Arg His
210             215             220
Arg Ala His Arg His Ala Gln Asp Ser Ser Lys Glu Gly Lys Glu Gly
225             230             235                         240
Thr Ala Pro Val Leu Val Pro Lys Gly Glu Arg Arg Ala Arg His Arg
             245             250             255
Gly Pro Arg Thr Gly Pro Arg Glu Thr Glu Asn Ser Glu Glu Pro Thr
             260             265             270
Arg Arg His Arg Ala Lys His Lys Val Pro Pro Thr Leu Glu Pro Pro
275             280             285
Glu Arg Glu Val Ala Glu Lys Glu Ser Asn Val Val Glu Gly Asp Lys
     290             295             300
Glu Thr Arg Asn His Gln Pro Lys Glu Pro Arg Cys Asp Leu Glu Ala
305             310             315             320
Ile Ala Val Thr Gly Val Gly Ser Leu His Met Leu Pro Ser Thr Cys
             325             330             335
Leu Gln Lys Val Asp Glu Gln Pro Glu Asp Ala Asp Asn Gln Arg Asn
             340             345             350
Val Thr Arg Met Gly Ser Gln Pro Ser Asp Pro Ser Thr Thr Val His
         355             360             365
Val Pro Val Thr Leu Thr Gly Pro Pro Gly Glu Ala Thr Val Val Pro
     370             375             380
Ser Ala Asn Thr Asp Leu Glu Gly Gln Ala Glu Gly Lys Lys Glu Ala
385             390             395             400
Glu Ala Asp Asp Val Leu Arg Arg Gly Pro Arg Pro Ile Val Pro Tyr
             405             410             415
Ser Ser Met Phe Cys Leu Ser Pro Thr Asn Leu Leu Arg Arg Phe Cys
             420             425             430
His Tyr
```

( 2 ) INFORMATION FOR SEQ ID NO:3:

( i ) SEQUENCE CHARACTERISTICS:
        ( A ) LENGTH: 434 amino acids (B) TYPE: amino acid
(C) STRANDEDNESS:
(D) TOPOLOGY: linear (xi) SEQUENCE DESCRIPTION: SEQ ID NO:3:

```
Asp Asn Leu Ala Asn Ala Gln Glu Leu Thr Lys Asp Glu Glu Glu Met
1               5                   10                  15

Glu Glu Ala Ala Asn Gln Lys Leu Ala Leu Gln Lys Ala Lys Glu Val
            20                  25                  30

Ala Glu Val Ser Pro Met Ser Ala Ala Asn Ile Ser Ile Ala Ala Arg
        35              40                  45

Gln Gln Asn Ser Ala Lys Ala Arg Ser Val Trp Glu Gln Arg Ala Ser
    50              55                  60

Gln Leu Arg Leu Gln Asn Leu Arg Ala Ser Cys Glu Ala Leu Tyr Ser
65              70                  75                  80

Glu Met Asp Pro Glu Glu Arg Leu Arg Phe Ala Thr Thr Arg His Leu
                85                  90                  95

Arg Pro Asp Met Lys Thr His Leu Asp Arg Pro Leu Val Val Glu Leu
            100                 105                 110

Gly Arg Asp Gly Ala Arg Gly Pro Val Gly Gly Lys Ala Arg Pro Glu
        115                 120                 125

Ala Ala Glu Ala Pro Glu Gly Val Asp Pro Pro Arg Arg His His Arg
    130                 135                 140

His Arg Asp Lys Asp Lys Thr Pro Ala Ala Gly Asp Gln Asp Arg Ala
145                 150                 155                 160

Glu Ala Pro Lys Ala Glu Ser Gly Glu Pro Gly Ala Arg Glu Glu Arg
                165                 170                 175

Pro Arg Pro His Arg Ser His Ser Lys Glu Ala Ala Gly Pro Pro Glu
            180                 185                 190

Ala Arg Ser Glu Arg Gly Arg Gly Pro Gly Pro Glu Gly Gly Arg Arg
        195                 200                 205

His His Arg Arg Gly Ser Pro Glu Glu Ala Ala Glu Arg Glu Pro Arg
    210                 215                 220

Arg His Arg Ala His Arg His Gln Asp Pro Ser Lys Glu Cys Ala Gly
225                 230                 235                 240

Ala Lys Gly Glu Arg Arg Ala Arg His Arg Gly Gly Pro Arg Ala Gly
                245                 250                 255

Pro Arg Glu Ala Glu Ser Gly Glu Glu Pro Ala Arg Arg His Arg Ala
            260                 265                 270

Arg His Lys Ala Gln Pro Ala His Glu Ala Val Glu Lys Glu Thr Thr
        275                 280                 285

Glu Lys Glu Ala Thr Glu Lys Glu Ala Glu Ile Val Glu Ala Asp Lys
    290                 295                 300

Glu Lys Glu Leu Arg Asn His Gln Pro Arg Glu Pro His Cys Asp Leu
305                 310                 315                 320

Glu Thr Ser Gly Thr Val Thr Val Gly Pro Met His Thr Leu Pro Ser
                325                 330                 335

Thr Cys Leu Gln Lys Val Glu Glu Gln Pro Glu Asp Ala Asp Asn Gln
            340                 345                 350

Arg Asn Val Thr Arg Met Gly Ser Gln Pro Pro Asp Pro Asn Thr Ile
        355                 360                 365

Val His Ile Pro Val Met Leu Thr Gly Pro Leu Gly Glu Ala Thr Val
    370                 375                 380

Val Pro Ser Gly Asn Val Asp Leu Glu Ser Gln Ala Glu Gly Lys Lys
385                 390                 395                 400
```

| | | | | | | | | | | | | | | |
|---|---|---|---|---|---|---|---|---|---|---|---|---|---|---|
| Glu | Val | Glu | Ala | Asp 405 | Asp | Val | Met | Arg | Ser 410 | Gly | Pro | Arg | Pro 415 | Ile | Val |
| Pro | Tyr | Ser | Ser 420 | Met | Phe | Cys | Leu | Ser 425 | Pro | Thr | Asn | Leu | Leu 430 | Arg | Arg |
| Phe | Cys | | | | | | | | | | | | | | |

( 2 ) INFORMATION FOR SEQ ID NO:4:

( i ) SEQUENCE CHARACTERISTICS:
        ( A ) LENGTH: 288 amino acids
        ( B ) TYPE: amino acid
        ( C ) STRANDEDNESS:
        ( D ) TOPOLOGY: linear ( x i ) SEQUENCE DESCRIPTION: SEQ ID NO:4:

| | | | | | | | | | | | | | | |
|---|---|---|---|---|---|---|---|---|---|---|---|---|---|---|
| Met 1 | Lys | Asp | Arg | Thr 5 | Gln | Glu | Leu | Arg | Thr 10 | Ala | Lys | Asp | Ser | Asp 15 | Asp |
| Asp | Asp | Asp | Val 20 | Thr | Val | Thr | Val | Asp 25 | Arg | Asp | Arg | Phe | Met 30 | Asp | Glu |
| Phe | Phe | Glu 35 | Gln | Val | Glu | Glu | Ile 40 | Arg | Gly | Phe | Ile | Asp 45 | Lys | Ile | Ala |
| Glu | Asn 50 | Val | Glu | Glu | Val 55 | Lys | Arg | Lys | His | Ser 60 | Ala | Ile | Leu | Ala | Ser |
| Pro 65 | Asn | Pro | Asp | Glu 70 | Lys | Thr | Lys | Glu | Glu 75 | Leu | Glu | Glu | Leu | Met 80 | Ser |
| Asp | Ile | Lys | Lys 85 | Thr | Ala | Asn | Lys | Val 90 | Arg | Ser | Lys | Leu | Lys 95 | Ser | Ile |
| Glu | Gln | Ser | Ile 100 | Glu | Gln | Glu | Glu | Gly 105 | Leu | Asn | Arg | Ser | Ser 110 | Ala | Asp |
| Leu | Arg | Ile 115 | Arg | Lys | Thr | Gln | His 120 | Ser | Thr | Leu | Ser | Arg 125 | Lys | Phe | Val |
| Glu | Val | Met 130 | Ser | Glu | Tyr | Asn 135 | Ala | Thr | Gln | Ser | Asp 140 | Tyr | Arg | Glu | Arg |
| Cys 145 | Lys | Gly | Arg | Ile | Gln 150 | Arg | Gln | Leu | Glu | Ile 155 | Thr | Gly | Arg | Thr | Thr 160 |
| Thr | Ser | Glu | Glu | Leu 165 | Glu | Asp | Met | Leu | Glu 170 | Ser | Gly | Asn | Pro | Ala 175 | Ile |
| Phe | Ala | Ser | Gly 180 | Ile | Ile | Met | Asp | Ser 185 | Ser | Ile | Ser | Lys | Gln 190 | Ala | Leu |
| Ser | Glu | Ile 195 | Glu | Thr | Arg | His | Ser 200 | Glu | Ile | Ile | Lys | Leu 205 | Glu | Asn | Ser |
| Ile | Arg 210 | Glu | Leu | His | Asp | Met 215 | Phe | Met | Asp | Met | Ala 220 | Met | Leu | Val | Glu |
| Ser 225 | Gln | Gly | Glu | Met | Ile 230 | Asp | Arg | Ile | Glu | Tyr 235 | Asn | Val | Glu | His | Ala 240 |
| Val | Asp | Tyr | Val | Glu 245 | Arg | Ala | Val | Ser | Asp 250 | Thr | Lys | Lys | Ala | Val 255 | Lys |
| Tyr | Gln | Ser | Lys 260 | Ala | Arg | Arg | Lys | Lys 265 | Ile | Met | Ile | Ile | Ile 270 | Cys | Cys |
| Val | Ile | Leu 275 | Gly | Ile | Ile | Ile | Ala 280 | Ser | Thr | Ile | Gly | Gly 285 | Ile | Phe | Gly |

METHODS AND COMPOSITIONS FOR SCREENING FOR PRESYNAPTIC CALCIUM CHANNEL BLOCKERS

TECHNICAL FIELD

The present invention is generally directed toward assays and compositions for identifying compounds that block neurotransmitter release. This invention is more particularly related to screening candidate compounds for the ability to block presynaptic calcium channels.

BACKGROUND OF THE INVENTION

Neurotransmitter release at the presynaptic terminal of neurons is primarily initiated by the entry of calcium through voltage-gated calcium channels (Smith and Augustine, *Trends Neurosci.* 11:458–464, 1988; Robitaille et al., *Neuron* 5:773–779, 1990). Exocytosis of synaptic vesicles occurs at specialized regions of the nerve terminal called active zones. These zones may contain clusters of presynaptic calcium channels that supply calcium for neurotransmitter release (Pumplin et al., *Proc. Natl. Acad. Sci. USA* 78:7210–7214, 1981; Pumplin, *J. Neurocytol.* 12:317–323, 1983; Zucker, *J. Physiol.* 87:25–36, 1993). Synaptic transmission is initiated within 200 µs after the arrival of the action potential at the synaptic terminal. The brief rise in $Ca^{++}$ concentration to the level necessary for exocytosis likely occurs only in proximity to the calcium channels (Llinas et al., *Biophys. J.* 33:289–322; Cope and Mendell, *J. Neurosci.* 47:469–478, 1982).

A combination of electrophysiological and pharmacological criteria have defined four main types of high-voltage-activated calcium channels that are widely distributed in mammalian neurons. These are ω-conotoxin-GVIA-sensitive N-type calcium channels, ω-agatoxin IVA-sensitive and ω-conotoxin-MVIIC-sensitive P-type and Q-type calcium channels, and dihydropyridine-sensitive L-type calcium channels (for reviews see Bean, *Annu. Rev. Physiol.* 51:367–384, 1989; Hess, *Ann. Rev. Neurosci.* 13:337–356, 1990; Tsien et al., *Trends Pharmac. Sci.* 12:349–354, 1991; Miller, *J. Biol. Chem.* 267:1403–1406, 1992; Zhang et al., *Neuropharmacology* 32:1075–1088, 1993). Several lines of evidence indicate that N-type channels, at least in part, are responsible for the calcium influx that triggers transmitter release in many neurons. Antibodies against ω-conotoxin GVIA (ωCTx GVIA) or fluorescent toxin derivatives label active zones on the terminals of motor neurons at the frog neuromuscular junction (Robitaille et al., *Neuron* 5:773–779, 1990; Cohen et al., *J. Neurosci* 1:1032–1039, 1991). Immunocytochemical studies with specific site-directed anti-peptide antibodies indicate that N-type channels are located along the length of dendrites and in synapses formed on the dendrites of many brain neurons (Westenbroek et al., *Neuron* 9:1099–1115, 1992). In contrast, antibodies to L-type channels recognize calcium channels in cell bodies and proximal dendrites, but give no detectable staining of presynaptic terminals in brain (Ahlijanian et al., *Neuron* 4:819–832, 1990). In addition, ω-CTx-GVIA inhibits transmitter release in a variety of mammalian neuronal preparations (Hirning et al., *Science* 239:57–60, 1988; Horne and Kemp, *Br. d. Pharmacol* 103:1733–1739, 1991; Takahashi and Momiyama, *Nature* 366:156–158, 1993; Luebke et al., *Neuron* 11:895–902, 1993; Turner et al., *Proc. Natl. Acad Sci. USA* 90:9518–9522, 1993; Wheeler et al., *Science* 264:107–111, 1994), thus supporting the hypothesis that N-type channels play a role in controlling neurotransmitter release in the central nervous system.

Molecular cloning has identified the primary structures of the main pore-forming α1 subunit of five distinct classes of calcium channels (classes A, B, C, D, and E) found in rat brain. Cloned neuronal $α1_C$ and $α1_D$ subunits are components of L-type channels, while the $α1_B$ subunit is a component of N-type channels (Dubel et al., *Proc. Natl. Acad. Sci. USA* 89:5058–5062, 1992; Williams et al., *Neuron* 8:71–84, 1992a; Williams et al., *Science* 257:389–395, 1992b; Westenbroek et al., *Neuron* 9:1099–1115, 1992; Stea et al., *Neuropharmacology* 32:1103–1116, 1993). $α1_A$ encodes Q-type calcium channels and may also encode P-type calcium channels (Snutch and Reiner, *Curr. Opin. Neurobiol.* 2:247–253, 1992; Tsien et al., *Trends Pharmac. Sci.* 12:349–354, 1991; Mori et al., *Nature* 350:398–402, 1991; Sather et al., *Neuron* 11:291–303, 1993; Zhang et al., *Neuropharmacology* 32:1075–1088, 1993). The deduced amino acid sequence of $α1_b$ shares overall structural features with other calcium channel α1 subunits. It is composed of four predominantly hydrophobic homologous domains (I–IV) that are linked by intracellular hydrophilic loops of various lengths.

The traditional approach to blocking neurotransmitter release has been to use compounds that bind to the neuronal voltage-gated calcium channels in a manner such that calcium entry through the channels is blocked. One of the difficulties in such an approach is the lack of specificity. As noted above, voltage-activated calcium channels that are found at sites in the body other than at presynaptic terminals appear to share structural features responsible for the movement of calcium through the channels. Accordingly, compounds that interact with the pore portion of calcium channels to block calcium entry into presynaptic nerve terminals will also block calcium channels at other sites throughout the body. Therefore, the traditional compounds for blocking neurotransmitter release have undesired side effects due to the blockade of additional calcium channels.

Due to the limited success for previously suggested compounds for the inhibition of neurotransmitter release, there is a need in the art for methods and compositions to screen for new inhibitors with specificity for presynaptic voltage-gated calcium channels. The present invention fulfills this need, and further provides other related advantages.

SUMMARY OF THE INVENTION

Current compounds in the art for blocking neurotransmitter release act by inhibiting the calcium influx through calcium channels that triggers transmitter release. As noted above, this approach suffers from problems associated with the inhibition of calcium channels at sites other than presynaptic terminals of neurons. An advantage of the methods and compositions of the present invention is that compounds are screened for the ability to inhibit the docking of presynaptic vesicles to presynaptic calcium channels, rather than for the ability to inhibit calcium influx through the channels.

Briefly stated, the present invention provides a variety of methods and compositions related to screening compounds for the ability to inhibit the interaction between presynaptic calcium channels and presynaptic vesicles (e.g., by the ability to bind to a selected presynaptic calcium channel-like peptide). In one aspect, the present invention provides peptides derived from, or based upon, a selected portion of a presynaptic calcium channel amino acid sequence. In one embodiment, the peptide consists essentially of the amino acid sequence of FIG. 11A from alanine, amino acid 773, to aspartic acid, amino acid 859. In another embodiment, the peptide consists essentially of the amino acid sequence of FIG. 11A from glutamic acid, amino acid 718, to aspartic acid, amino acid 859. In another embodiment, the peptide consists essentially of the amino acid sequence of FIG. 11A from glutamic acid, amino acid 718, to cysteine, amino acid 1141. In another embodiment, the peptide consists essentially of the amino acid sequence of FIG. 11A from an amino acid positioned between glutamic acid, amino acid 718, and alanine, amino acid 773, to an amino acid positioned between aspartic acid, amino acid 859, and cysteine, amino acid 1141. In another embodiment, the peptide consists essentially of an amino acid sequence of between 87 to 424 amino acid residues in length, wherein the amino acid sequence contains an amino acid sequence having at least 60% sequence similarity with the amino acid sequence of FIG. 11A from alanine, amino acid 773, to aspartic acid, amino acid 859.

In another embodiment the peptide consists essentially of the amino acid sequence of FIG. 11B from alanine, amino acid 772, to aspartic acid, amino acid 858. In another embodiment, the peptide consists essentially of the amino acid sequence of FIG. 11B from glutamic acid, amino acid 717, to aspartic acid, amino acid 858. In another embodiment, the peptide consists essentially of the amino acid sequence of FIG. 11B from glutamic acid, amino acid 717, to cysteine, amino acid 1143. In another embodiment, the peptide consists essentially of the amino acid sequence of FIG. 11B from an amino acid positioned between glutamic acid, amino acid 717, and alanine, amino acid 772, to an amino acid positioned between aspartic acid, amino acid 858, and cysteine, amino acid 1143. In another embodiment, the peptide consists essentially of an amino acid sequence of between 87 to 427 amino acid residues in length, wherein the amino acid sequence contains an amino acid sequence having at least 60% sequence similarity with the amino acid sequence of FIG. 11B from alanine, amino acid 772, to aspartic acid, amino acid 858.

In yet another embodiment, the peptide is a syntaxin-like peptide and consists essentially of the amino acid sequence of FIG. 12 from isoleucine, amino acid 181, to glycine, amino acid 288.

In another aspect, the present invention provides methods of screening for compounds that inhibit the interaction between presynaptic calcium channel and presynaptic vesicles. In one embodiment, the method comprises the step of: (a) contacting a presynaptic calcium channel-like peptide with a candidate compound under conditions sufficient to permit binding between the peptide and the candidate compound, and (b) detecting the presence or absence of binding between the peptide and the candidate compound, thereby determining whether the candidate compound bound to the peptide.

In another embodiment, the method comprises the steps of: (a) incubating a candidate compound, a presynaptic calcium channel-like peptide, and a syntaxin-like peptide under conditions sufficient to permit binding between the two peptides, and (b) detecting the presence or absence of binding between the two peptides, thereby determining whether the candidate compound inhibited the binding.

In another embodiment, the method comprises the steps of: (a) incubating a presynaptic calcium channel-like peptide and a candidate compound under conditions sufficient to permit binding between the peptide and the candidate compound, to form a reaction mixture, (b) contacting a syntaxin-like peptide with the reaction mixture under conditions sufficient to permit binding between the two peptides, and (c) detecting the presence or absence of binding between the two peptides, thereby determining whether the candidate compound inhibited the binding.

In another embodiment, the method comprises the steps of: (a) incubating a candidate compound, a peptide according to any one of claims 1–10, and syntaxin under conditions sufficient to permit binding between the peptide and the syntaxin, and (b) detecting the presence or absence of binding between the peptide and the syntaxin, thereby determining whether the candidate compound inhibited the binding.

In yet another embodiment, the method comprises the steps of: (a) incubating a peptide according to any of claims 1–10 and a candidate compound under conditions sufficient to permit binding between the peptide and the candidate compound, to form a reaction mixture, (b) contacting syntaxin with the reaction mixture under conditions sufficient to permit binding between the peptide and the syntaxin, and (c) detecting the presence or absence of binding between the peptide and the syntaxin, thereby determining whether the candidate compound inhibited the binding.

These and other aspects of the present invention will become evident upon reference to the following detailed description and attached drawings.

Figure 10A:
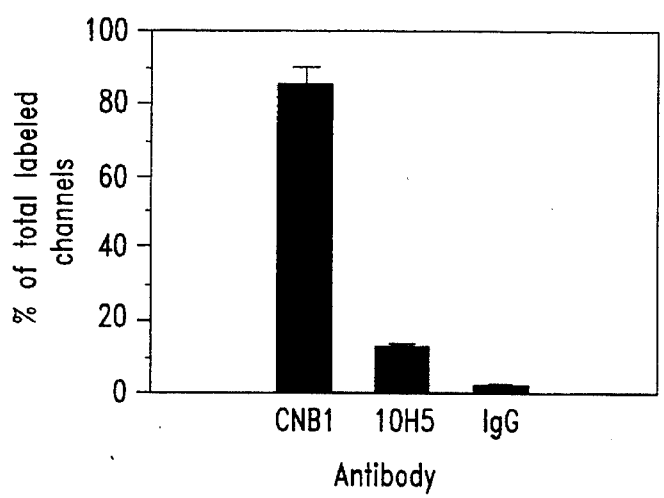
FIGS. 10A, 10B and 10C contain graphs demonstrating the inhibition of N-type calcium channel binding to syntaxin 1A by the 87 amino acid binding peptide. The graph in FIG. 10A shows the extent of immunoprecipitation of $\alpha 1_B$ and $\alpha 1_B$-syntaxin complex. The class B N-type calcium channels in synaptic membranes were solubilized with digitonin and partially purified by wheat germ agglutinin (WGA)-Sepharose affinity chromatography. The calcium channels were labeled with 500 fmol $[^{125}I]Tyr^{22}$-ω-CTx-GVIA and immunoprecipitated with CNB1 (anti-$\alpha 1_B$), 10H5 (anti-syntaxin), and control mouse IgG as indicated. The immunoprecipitation data are expressed as a percentage of the total labeled channels.
Figure 10B:
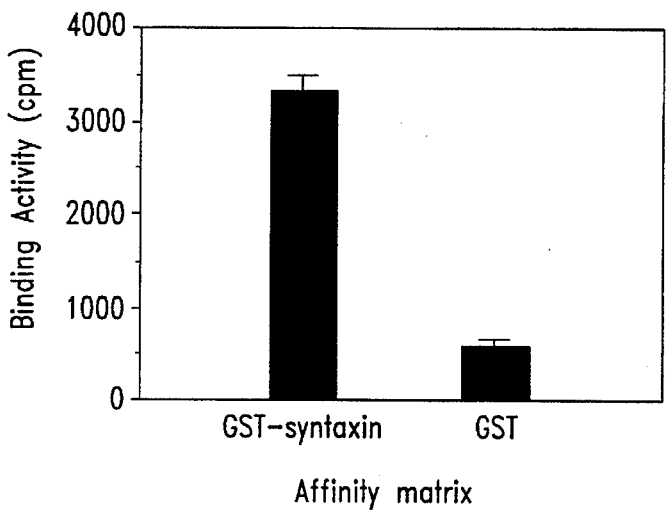

The graph in FIG. 10B shows the direct interaction of $^{125}I$-ω-CTx-GVIA receptor and GST-syntaxin. Equal amounts (cpm) of $[^{125}I]$-ω-CTx-GVIA-labeled N-type calcium channels were incubated with affinity matrices containing GST-syntaxin or GST for 3 hr. The beads were washed for three times with PBS, and the amount of bound receptors was assessed by direct counting. The counts from three independent binding data were averaged.

Figure 10C:
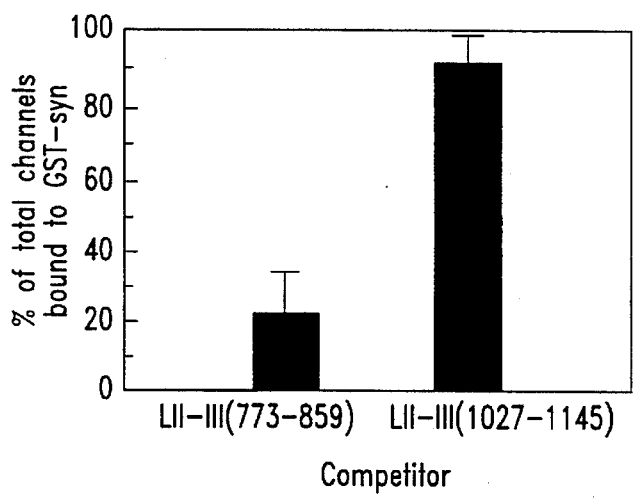

The graph in FIG. 10C displays results of binding competition assays. The binding assays were performed as in FIG. 10B except that the competing peptides, His-$L_{II-III}$ (733–859) or His-$L_{II-III}$ (1027–1145) were present. The reduction of binding activity was expressed as a percentage of total binding of labeled receptors to GST-syntaxin in the absence of any competing peptide. The data were averaged from three independent experiments.

FIGS. 11A and 11B show an alignment of loop $L_{II-III}$ (710–1143) amino acid sequences of rat (FIG. 11A; SEQ. ID NO: 2) and human (FIG. 11B; SEQ. ID No: 3) N-type calcium channels. The sequences have been aligned to maximize the sequence similarity.

FIG. 12 depicts the entire amino acid sequence (1–288; SEQ. ID NO: 4) of rat syntaxin 1A.

DETAILED DESCRIPTION OF THE INVENTION

The identification of calcium channel blockers that specifically inhibit the presynaptic calcium channels involved in release of neurotransmitters, such as glutamate, at excitatory synapses in the central nervous system would be therapeutically beneficial (e.g., in preventing the neuronal cell death that accompanies cerebral ischemia). As described above, compounds that block the calcium conductance activity of these channels are not specific. The present invention provides a screening approach, for compounds which prevent neurotransmitter release triggered by presynaptic calcium channels, that is based on inhibition of the docking of presynaptic vesicles to active zones containing the presynaptic calcium channels.

The disclosure of the present invention shows that presynaptic calcium channels possess a site for binding syntaxin, a protein anchored in the presynaptic plasma membrane, and that this site has a number of uses, including to screen for compounds that block neurotransmitter release. Compounds that inhibit syntaxin binding to the site (e.g., by the compound occupying the site) will interfere with the interaction between presynaptic calcium channels and presynaptic vesicles docked to syntaxin. With the methods and compositions of the present invention, candidate compounds may be screened for those that interrupt the interaction between presynaptic calcium channels and synaptic vesicles by interaction with the herein disclosed target site, which is on the calcium channel but is not involved in calcium influx itself. Thus, the present invention permits the identification of compounds with the desirable properties that, although calcium would still enter through the channel, transmitter release would not occur because the synaptic vesicle would not be properly docked to respond to the locally-increased calcium concentration.

As shown by the disclosure provided herein, presynaptic calcium channels (also known as "N-type") possess amino acid sequences that interact specifically with syntaxin, a presynaptic plasma membrane protein. In particular, syntaxin is shown to directly interact with the cytoplasmic loop ($L_{II-III}$) between homologous repeats (domains) II and III of N-type calcium channels. Loop $L_{II-III}$ is a sequence of about 428 amino acids composed from about residues 718 to about 1145 of the α1 subunit of N-type calcium channels. While the entire $L_{II-III}$ sequence may be used, it is not required as portions of the sequence will suffice. For example, an amino-terminal sequence of about 142 amino acids (from about residues 718 to 859 in FIG. 11A) interact with syntaxin. Further, portions of this amino-terminal sequence may be used for interaction with syntaxin. For example, a sequence of about 87 amino acids (from about residues 773 to 859) interact specifically with syntaxin.

Similarly, while the entire syntaxin protein may be used, it is not required as portions of the sequence will suffice. For example, a carboxyl-terminal sequence of about 108 amino acids (from about residues 181 to 288 in FIG. 12) interacts with $L_{II-III}$ or portions thereof. It will be evident to those of ordinary skill in the art that based on the disclosure provided herein that smaller segments of syntaxin may be identified that retain the characteristics high affinity interaction described herein between syntaxin and N-type calcium channels.

Based on the foregoing, the present invention discloses peptides useful for targeting compounds to disrupt the interaction between syntaxin and N-type calcium channels (e.g., to prevent neurotransmitter release triggered by presynaptic calcium channels). Peptides may be produced in a variety of ways well known to those in the art. For example, peptides may be derived from native proteins, prepared by synthetic chemistry methodology (including automated peptide synthesis, e.g., using an instrument available from Applied Biosystems, Inc., Foster City, Calif.), or produced by recombinant DNA techniques (including as fusion proteins expressed in microorganisms such as bacteria). Preferred peptides include those which correspond to the amino acid sequences in FIG. 11A from amino acid 718 to 1141 or from 718 to 859, and particularly preferred is from 773 to 859.

Based upon the present, disclosure, it will be evident to those in the art that useful peptides may be created which contain a sequence identical, or similar, to that of amino acids 773-859 in FIG. 11A. For example, the amino terminus of such a peptide may begin at any of the amino acids positioned between (as used herein "between" includes the recited amino acids) amino acid 718 to 773 and the carboxyl terminus may end at any of the amino acids positioned between amino acid 859 to 1141. Alternatively, for example, a peptide may be similar in length to the peptides of amino acids from 718 to 1141 or 773 to 859 (i.e., have a length of about 87 to 424 amino acid residues) and contain an amino acid sequence having at least 60% sequence similarity with the amino acid sequence of FIG. 11A from amino acids 773 to 859. Particularly preferred peptides include those with about 65%, 70%, 75%, 80%, 85% or greater sequence similarity, and those with about 75%, 80%, 85% or greater sequence identity. Sequence similarity is based upon sequence identity plus conservative substitutions of amino acids. Conservative substitutions include interchanges of valine and isoleucine, leucine and isoleucine, aspartic acid and glutamic acid, and others of a similar nature. When such a peptide has more than 87 residues, the additional amino acids may have, but need not have, sequence similarity to the $L_{II-III}$ sequence. It will be evident to those in the art, when in possession of the present disclosure, that modifications (e.g., additions, deletions and substitutions) may be made to a particular peptide without substantially affecting the peptide's ability to act as a binding partner for syntaxin or a binding portion thereof.

Additional preferred peptides include the human amino acid sequences known in FIG. 11B that correspond to the sequences described above from FIG. 11A. For example, preferred peptides include those which correspond to the amino acid sequences in FIG. 11B from amino acid 717 to 1143 or from 717 to 858, and particularly preferred is from 772 to 858. The above discussion regarding variations on the preferred peptides from FIG. 11A is similarly applicable to the preferred peptides from FIG. 11B and is incorporated here by reference thereto. Other peptides with one or more additions, deletions or substitutions to the sequences described herein may be tested for syntaxin binding and compared to the results disclosed herein for certain preferred peptides. Based upon the results of tests of any other peptides, it will be readily apparent whether a particular peptide is suitable.

Similar to that described above for the calcium channel, an entire syntaxin protein may be used, but it is not required as portions of the sequence will suffice. The present invention discloses peptides that are less than an entire syntaxin amino acid sequence, yet still interact specifically with N-type calcium channel or portions thereof. An example of such a peptide is the sequence from amino acids 181 to 288 in FIG. 12.

The above-described presynaptic calcium channel peptides and variations therefrom that bind syntaxin or portion thereof (herein collectively termed "calcium channel-like peptides") may be used to screen for one or more compounds that inhibit the interaction between presynaptic calcium channels and presynaptic vesicles, as mediated by syntaxin. Assays for screening for such compounds may take a variety of formats, including direct and indirect (e.g., competition). In one embodiment, a candidate compound is tested for the ability to bind to a peptide of the type described above. For example, a candidate compound may be contacted with such a peptide that contains a reporter group. The reaction conditions (e.g., from about 1 min to 24 hr, at about 4° C. to about 37° C., and a pH of about 6 to 8.5) are sufficient to permit binding between the candidate compound and the peptide if binding is going to occur. The presence of binding is based upon the detection of the reporter group in association with the candidate compound.

In another embodiment a candidate compound is tested for the ability to inhibit the binding of a calcium channel-like peptide to a "syntaxin-like peptide" (i.e., a peptide selected from syntaxin peptides and variations therefrom that bind presynaptic calcium channel or calcium channel-like peptide). Either of the peptides may contain a reporter group to detect the binding between the peptides. Alternatively, for example, each peptide may contain a reporter group component that interact upon binding of the peptides. A candidate compound may be incubated simultaneously with both peptides. Alternatively, for example, a candidate compound is incubated with a calcium channel-like peptide to permit binding, if any, between the compound and the peptide. A syntaxin-like peptide is then contacted with the reaction mixture to permit binding between the calcium channel-like peptide and the syntaxin-like peptide. Where a candidate compound does not bind to the calcium channel-like peptide, the peptide will bind to the syntaxin-like peptide to the same extent as where the compound is absent (e.g., compound replaced in the first step with buffered solution). Thus, the presence of binding between the calcium channel-like peptide and the syntaxin-like peptide is indicative that the candidate compound did not bind to the former peptide. However, where a candidate compound does bind to the calcium channel-like peptide, the peptide is no longer available to bind to the syntaxin-like peptide. Thus, the absence of binding between the calcium channel-like peptide and the syntaxin-like peptide is indicative that the candidate compound does bind to the former peptide. All of the above discussion is equally applicable where a syntaxin-like peptide is replaced with syntaxin (i.e., a full length syntaxin protein).

Detection of binding between a compound and peptide or between two peptides may be accomplished by a variety of known techniques, including radioassays and enzyme linked assays. For detection purposes, a peptide can be directly labeled with a reporter group. Alternatively, a molecule (e.g., an antibody) that binds to a peptide or candidate compound can possess a reporter group. The reporter group can include radioisotopes, fluorophores, enzymes, luminescers, or dye particles. These land other labels are well known in the art and are described, for example, in the following U.S. Pat. Nos.: 3,766,162; 3,791,932; 3,817,837; 3,996,345; and 4,233,402.

The methods described herein may be used in a fully or partially automated format for high through-put screening of candidate compounds. For example, peptides may be utilized in a 96-well plate assay format with a reporter group amenable to automated analysis of the results. For example, the reporter group can be chosen from a variety of enzymes, including horseradish peroxidase, beta-galactosidase, alkaline phosphatase and glucose oxidase. The results of the reaction between an enzyme and its added substrate can be read optically in a 96-well plate reader.

Alternative formats, labeling and in general other modifications of the assays described above are within the scope of those in the art.

The methods and compositions of the present invention have a variety of uses. A particularly preferred use of the present invention is to screen for compounds that differentially modulate transmitter release versus current flow via calcium channels. Compounds may be identified that inhibit neurotransmitter release without blocking calcium influx. Although calcium would still enter through presynaptic calcium channels, transmitter release would not occur because the synaptic vesicles would not be properly docked to respond to the locally increased calcium concentration. Such compounds would effectively block release of neurotransmitters in the central nervous system and be useful in neuroprotection from excitotoxicity in many clinical settings, including the treatment of stroke, cognitive deficit related to cardiac surgery, and neuronal damage during acute epileptic episodes.

The following examples are offered by way of illustration and not by way of limitation.

EXAMPLES

Example 1

Construction and Expression of Recombinant GST-and His-Fusion Proteins

GST-Syntaxin 1A fusion proteins were generated by cloning amplified portions of the gene Corresponding to the full-length (2–289), N-terminal region (2–190) and C-terminal region (181–289) of rat syntaxin 1A (Yoshida et al., *J. Biol. Chem.* 267:24925–24928, 1992; Bennett et al., *Science* 257:255–259, 1992) were amplified by PCR. EcoRI and XhoI sites were included at the ends of the N-terminal and C-terminal oligonucleotide primers, respectively; stop codons were included in both oligonucleotides. The amplified material was then cloned into EcoRI/XhoI digested pGEX-4T expression vector (Pharmacia LKB Biotechnology) to obtain in-frame recombinant proteins fused to glutathione S-transferase (GST).

His-fusion proteins were generated by amplification from oligonucleotides flanking a series of cytoplasmic domains of the α1 subunit of rat class B N-type calcium channels and containing appropriate restriction sites and in-frame stop codons. Polymerase chain reaction was performed using $\alpha 1_B$ cDNA (rbB-1) as a template (Dubel et al., *Proc. Natl. Acad. Sci. USA* 89:5058–5062, 1992) to amplify the appropriate DNA fragments. The amplified products were directionally cloned into the pTrcHis C expression vector (Invitrogen) that codes for a stretch of 6 histidine residues immediately following the initiator codon. The His-fusion proteins containing various cytoplasmic domains/loops of calcium channel $\alpha 1_B$ were as follows: the cytoplasmic amino-terminal, His-NT (41–94); the loops between domains I and II, His-$L_{II-III}$ (357–483); the loops between domains II and III, His-$_{II-III}$ (718–1145); the loops between domains III and IV, His-$L_{II-III}$ (1418–1474); the cytoplasmic carboxyl-terminal I, His-CT-1 (1712–2068) and II, His-CT-2 (2044–2336); fragments between domains II and III, His-$L_{II-III}$ (718–859), His-$L_{II-III}$ (832–963), His-$L_{II-III}$ (940–1051), His-$L_{II-III}$ (1027–1145), His-$L_{II-III}$ (718–825), His-$L_{II-III}$ (744–859), His-$L_{II-III}$ (773–859); the cytoplasmic loops between domains II and III of $\alpha 1_A$ (723–868) and $\alpha 1_S$ (670–800). All constructs were verified by determining the DNA sequence.

Constructs were transformed into a protease-deficient strain, BL26 (Novagen). Fusion protein expression was obtained following the basic protocol of Smith and Johnson (*Gene* 67:31–40, 1988). In brief, fresh overnight cultures were diluted 1:10 in YT medium containing 100 µg/ml ampicillin and 2% glucose and incubated for 4 hr at 37° C. with shaking. After 2 hr of growth, isopropyl-β-D-thiogalactopyranoside (IPTG) was added to a final concentration of 0.5 mM. Bacterial cells were pelleted by centrifugation at 5000 x g for 10 min at 4° C. and resuspended in PBS buffer. The bacteria were lysed by mild sonication and solubilized by the addiction of Triton X-100 to final concentration of 1% followed by incubation for 30 min on ice.

Example 2

Screening of His-Fusion Proteins for Binding to GST-Syntaxin

Binding of the cytoplasmic domains/loops of calcium channels to GST-syntaxin fusion proteins was assayed. Approximately 2 µg of GST-syntaxin fusion proteins or GST alone was bound to glutathione-Sepharose 4B beads (Pharmacia) in PBS (140 mM NaCl, 2.7 mM KCl, 10.1 mM $Na_2HPO_4$, 1.8 mM $KF_2PO_4$, pH 7.3) containing 0.5% Triton X-100, 4 µg/ml pepstatin, 4 µg/ml aprotinin, 4 µg/ml leupeptin and 0.4 µM phenylmethylsulfonyl fluoride. The mixture was incubated at 4° C. for 1 hour with constant agitation. Following incubation, the beads were washed with PBS to remove uncoupled GST fusion proteins. Glutathione-Sepharose beads preincubated with similar amounts of GST-syntaxin or GST were added to the lysates containing 5–10 µg His-fusion proteins of the various cytoplasmic domains/loops of calcium channels and incubated with gentle mixing for 3 hr at 4° C. Following incubation, beads were washed three times in ice-cold PBS with 0.1% Triton X-100, three times in 50 mM Tris-HCl, pH 8.0/140 mM NaCl/0, 1% Triton X-100, and once in 50 mM Tris-HCl, pH 8.0.

Bound fusion proteins were eluted with 50 mM Tris-HCl, pH 8.0/15 mM glutathione for 20 min with gentle mixing and elutes were separated from the beads by centrifugation at 10,000 x g for 1 minute. Fusion proteins were electrophoresed on SDS/PAGE and transferred to nitrocellulose. Specific fusion proteins were detected by an ELC kit (Amersham) using either an anti-GST or T7-Tag antibody (Novagen). The T7-Tag antibody is a mouse monoclonal directed against the 12 amino acid leader peptide in the N-terminal of His-fusion proteins. To assess the quantity and quality of the His-fusion proteins used in binding assays, approximately 10% amount of lysates was examined by SDS/PAGE and immunoblotting. The amount of each fusion protein in the binding assays was estimated with a standard curve relating the intensity of the immunoblotting signal to the amount of a standard fusion protein.

Figure 1:
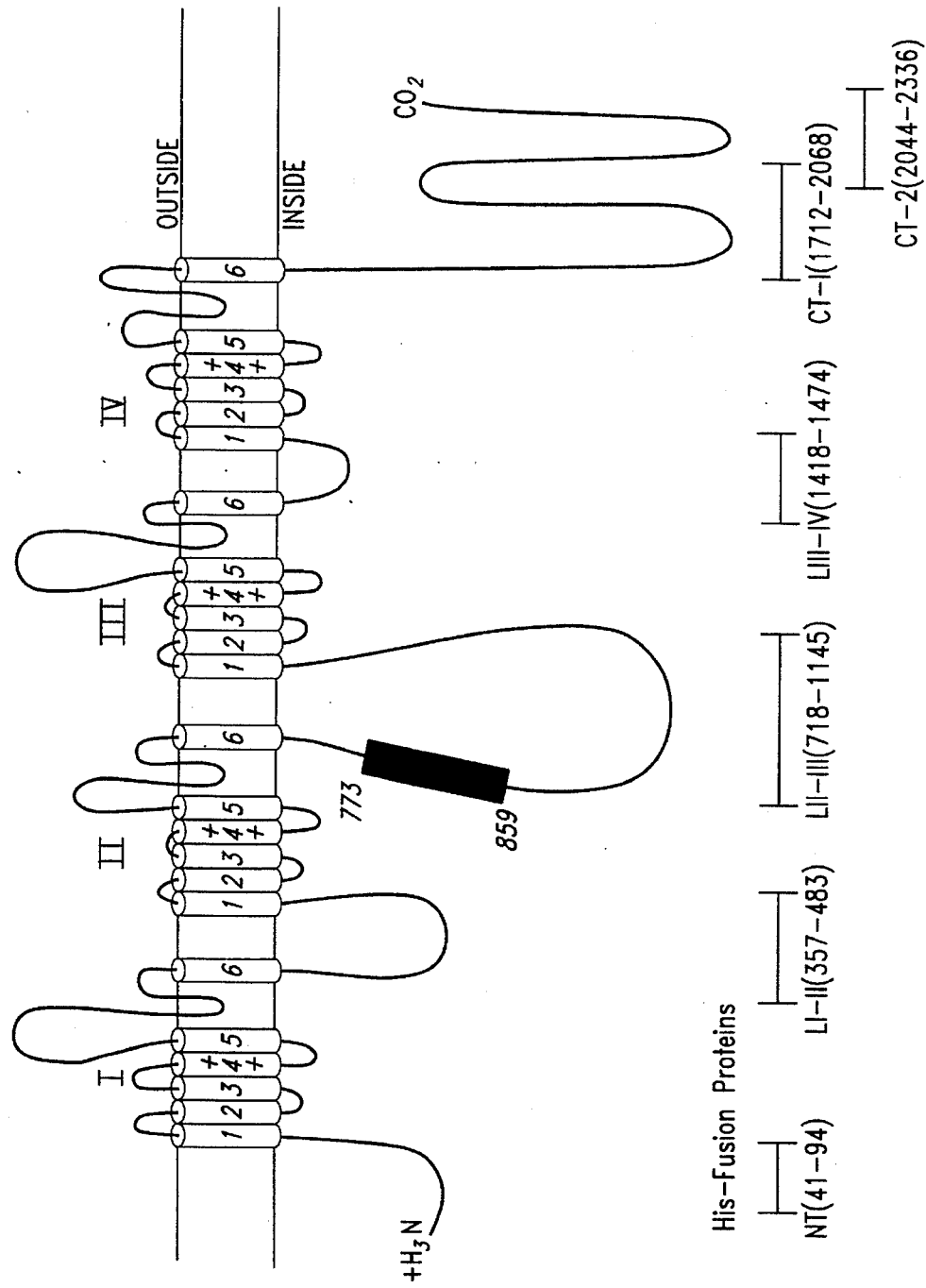
FIG. 1 is a drawing depicting the predicted topological structure of the α1 subunit of class B N-type calcium channels. The location of the recombinant His-fusion proteins of calcium channel cytoplasmic domains generated for binding studies are depicted. The filled-in rectangle indicates the region of interaction with syntaxin 1A.
Figure 2:
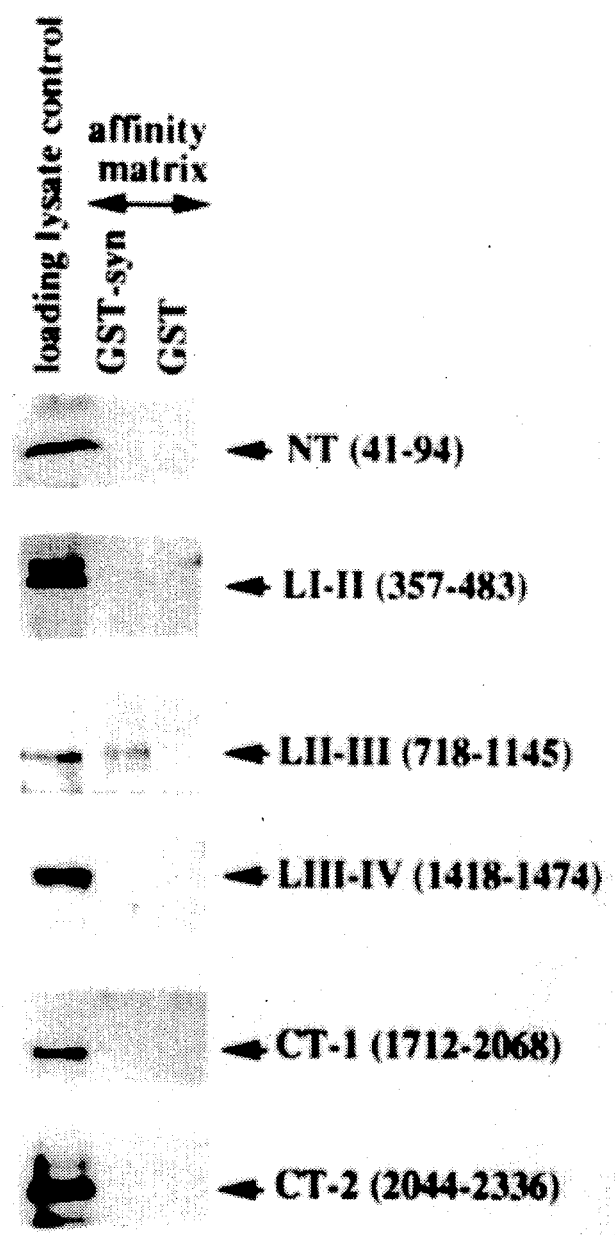
FIG. 2 is immunoblots (Panels A and B) that demonstrate the interaction of the cytoplasmic loop $L_{II-III}$ (718–1145) of $\alpha 1_B$ with syntaxin 1A. Approximately 2μg of GST-syntaxin (GST-syn) or GST coupled to glutathione-Sepharose 4B beads were incubated with 5–10 μg of the indicated various His-fusion proteins. Specifically-bound proteins were eluted by 15mM glutathione/50 mM Tris-HCl, pH 8, separated by SDS/PAGE, electrophoretically transferred to nitrocellulose, and probed for the presence of His-fusion proteins by immunoblotting with anti-T7-Tag antibody. Left lane, aliquots of lysates containing His-fusion proteins as indicated; center lane, eluate from GST-syntaxin affinity matrix; right lane, eluate from GST affinity matrix.

Interaction of His-$L_{II-III}$ (718–1145) with GST-syntaxin fusion protein was observed as a specific band as illustrated in FIG. 2 (middle lane, GST-syn). In contrast, no interaction was detected with GST alone (FIG. 2, right lane). All other His-fusion proteins containing the cytoplasmic loops, as well as the N- and C-terminal of $\alpha 1_B$, failed to demonstrate specific interaction with GST-syntaxin (FIG.2), even though comparable quantities of the expressed proteins were analyzed. These results suggest that there is a specific interaction between the cytoplasmic loop connecting domains II and III of $\alpha 1_B$ and syntaxin 1A.

Figure 3:
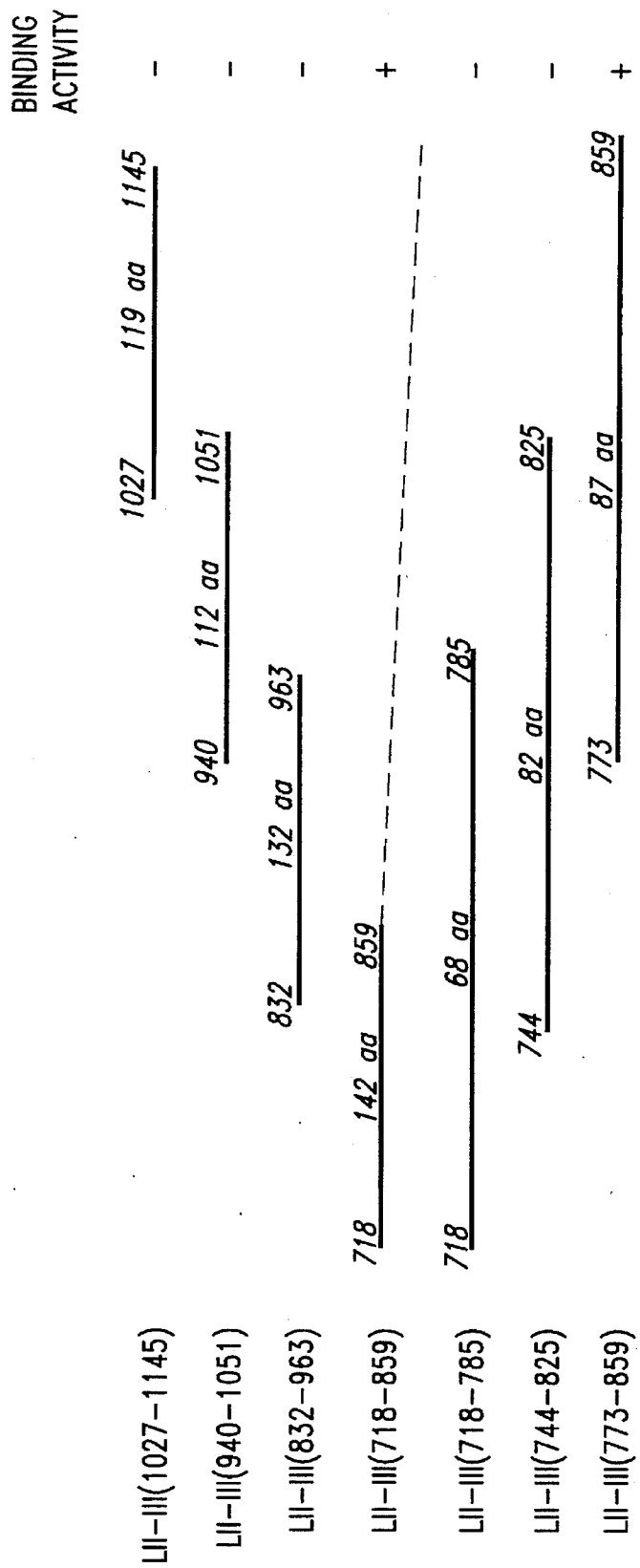
FIG. 3 is a schematic representation of the His-fusion proteins containing various sequences from the cytoplasmic loop $L_{II-III}$ (718–1145).
Figure 4A:
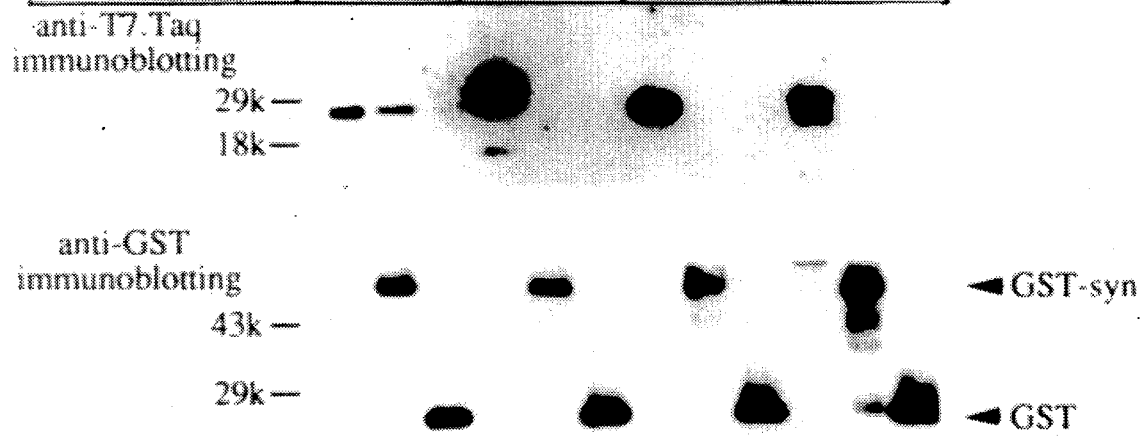
FIGS. 4A and 4B are immunoblot analyses of the interaction of fusion proteins containing sequences from loop $L_{II-III}$ (718–1145) with syntaxin 1A. The indicated His-fusion proteins were incubated with GST-syntaxin (GST-syn) and GST affinity matrices. Bound proteins were eluted and detected on immunoblots with anti-T7-Tag antibody. To normalize for the amounts of GST-syn or GST fusion proteins bound to affinity matrix and eluted, the blots were stripped and probed with anti-GST antibody.
Figure 4B:
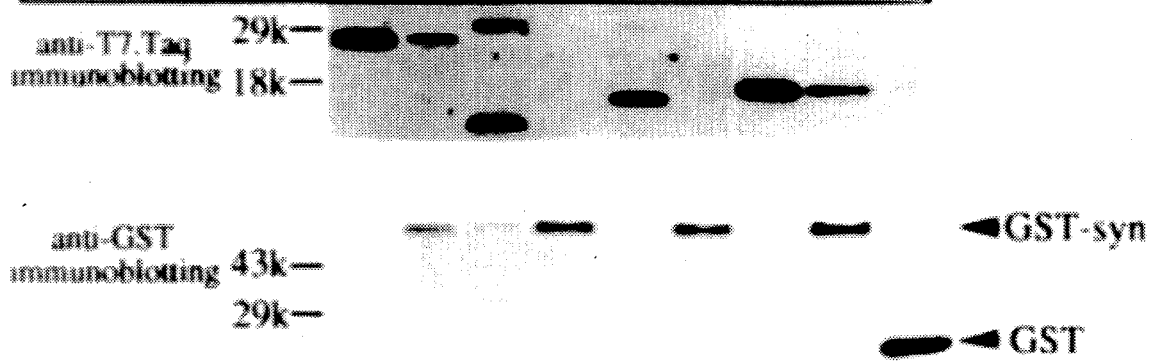
Figure 5:
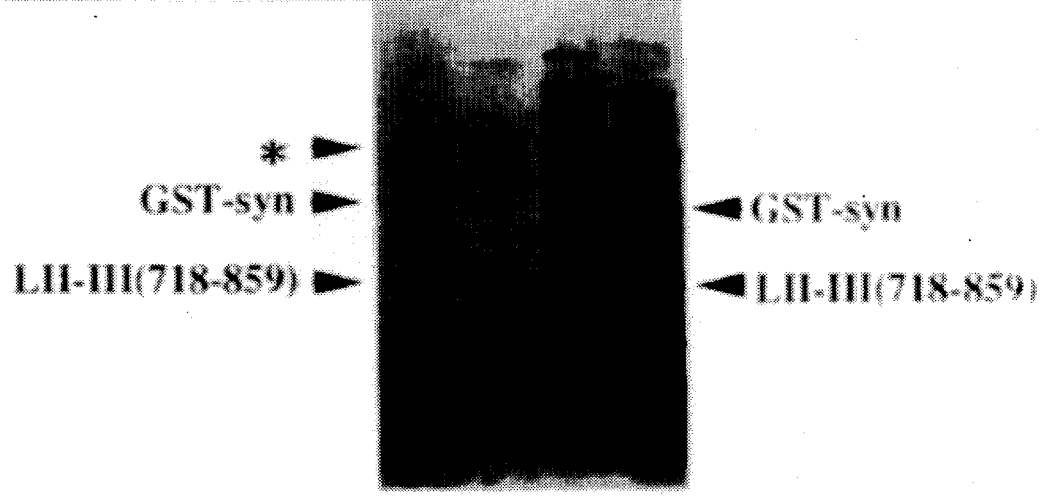
FIG. 5 is a Coomassie blue-stained polyacrylamide gel showing the specificity of the binding of GST-syntaxin to $L_{II-III}$ 718–859). Total bacterial lysate containing His-$L_{II-III}$ (718–859) fusion protein was incubated with glutathione-Sepharose-4B beads prebound by bacterial lysate containing GST-syntaxin fusion protein (GST-syn) or bacterial lysate without any fusion protein (control) as indicated. Complexes of GST-syntaxin and $L_{II-III}$ (718–859) were eluted and analyzed by SDS-PAGE and Coomassie blue staining. Migration positions of GST-syn, $L_{II-III}$ (718–859) and a non-specific glutathione-Sepharose binding bacterial protein of ~70 kDa (*) are indicated.
Figure 6:
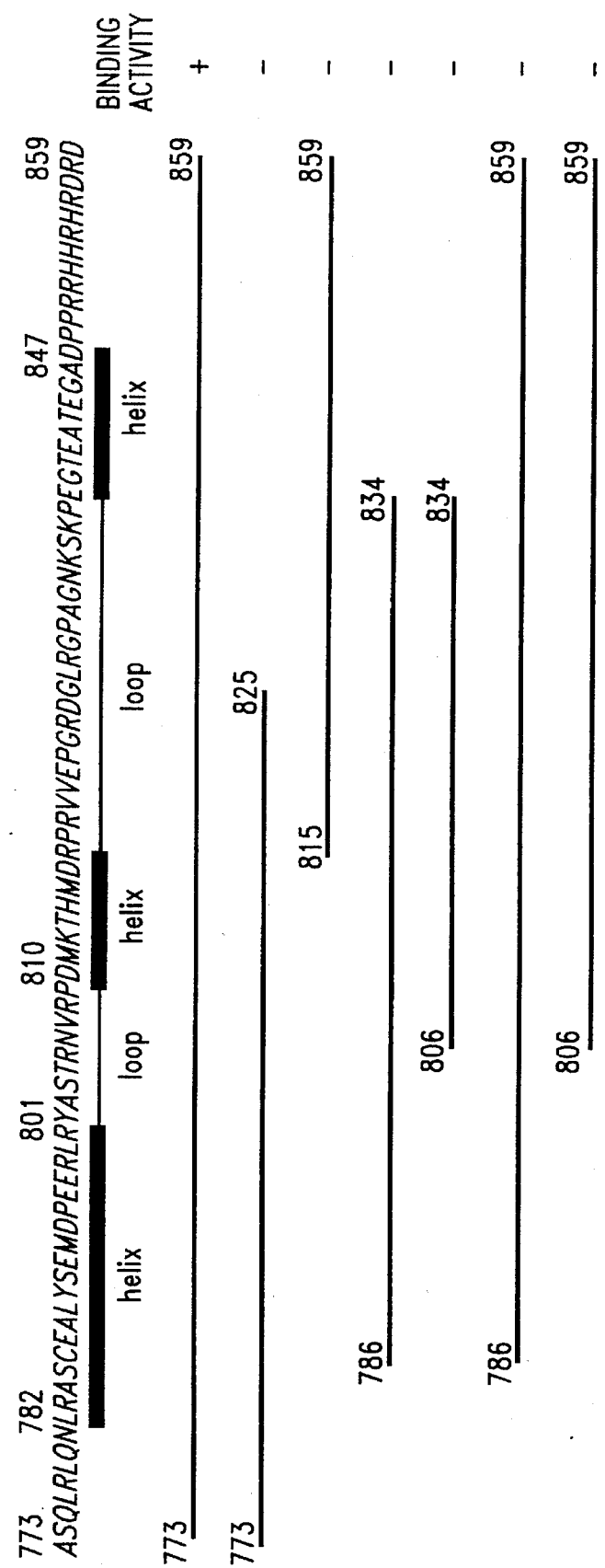
FIG. 6 shows a sequence analysis (SEQ. ID NO: 1) of the syntaxin-binding site and location of two overlapping helix-loop-helix motifs within the $L_{II-III}$ (773–859) region. Underneath the locations of amino acids used to generate six new His-fusion proteins are shown. The binding activity of each deleted fusion protein is listed in the right column.
Figure 7:
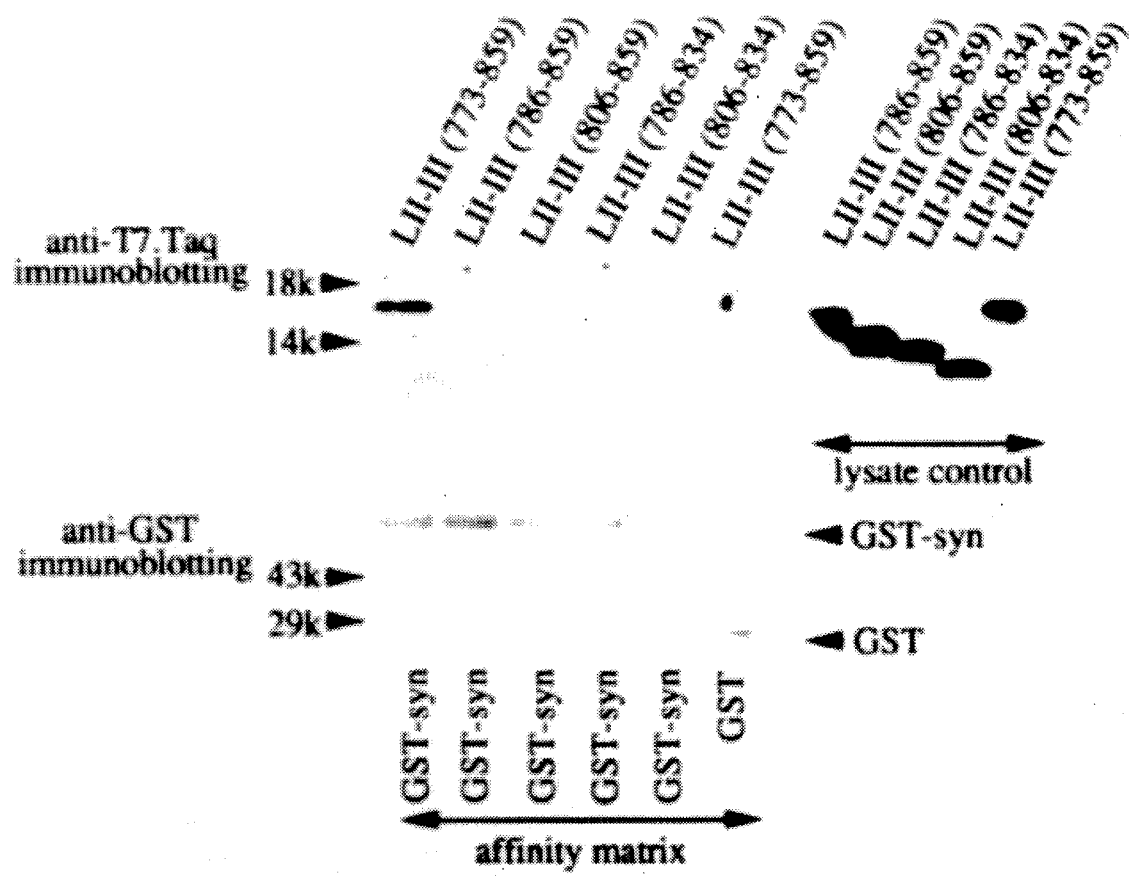
FIG. 7 is an immunoblot demonstrating that deletion mutants of the helix-loop-helix structure completely abolished syntaxin-binding activity. Approximately 5 µg of His-fusion proteins from four of the six deletion mutants shown in FIG. 6 and the complete 87-residue peptide (773–859) were incubated with affinity matrix containing 2 µg of GST-syn or GST. The bound His-fusion proteins were eluted and probed with anti-T7-Tag antibody (top). Controls for quantity and quality of His-fusion proteins are shown in the top right panel. The amounts of GST-syntaxin (GST-syn) or GST fusion proteins attached and eluted from matrix were determined by a second blotting with anti-GST antibody shown in bottom panel.

In order to investigate the minimum sequence requirements for binding to syntaxin 1A, a series of His-fusion proteins covering various lengths of $L_{II-III}$ were generated and analyzed for binding (FIG. 3). As shown in FIG. 4, the amino-terminal 142 amino acids (718–859) from $L_{II-III}$ are sufficient for binding to syntaxin 1A. Larger quantities of fusion proteins containing the remaining 286 amino acids (residues 860–1145) located in $L_{II-III}$ do not interact detectably with syntaxin 1A.

Further analysis of fusion proteins containing overlapping portions of the segment from residue 718–859 (FIG. 3) indicated that a sequence of 87 amino acids (773–859) of $\alpha 1_B$ was sufficient for interaction with syntaxin 1A (FIG. 4, right column). In contrast, the fusion peptides $L_{II-III}$ (718–785) and $L_{II-III}$ (744–825) do not interact specifically with syntaxin since no interaction was observed when they were incubated with the GST-syntaxin matrix (FIG. 4, middle columns). Thus, the first 56 residues (718–773) of $L_{II-III}$ are unlikely to be required for the syntaxin-binding site since His-$L_{II-III}$ (718–785) did not show any binding activity while His-$L_{II-III}$ (773–859) retained the full binding of the longer fusion peptide His-$L_{II-III}$ (718–859).

Figure 8:
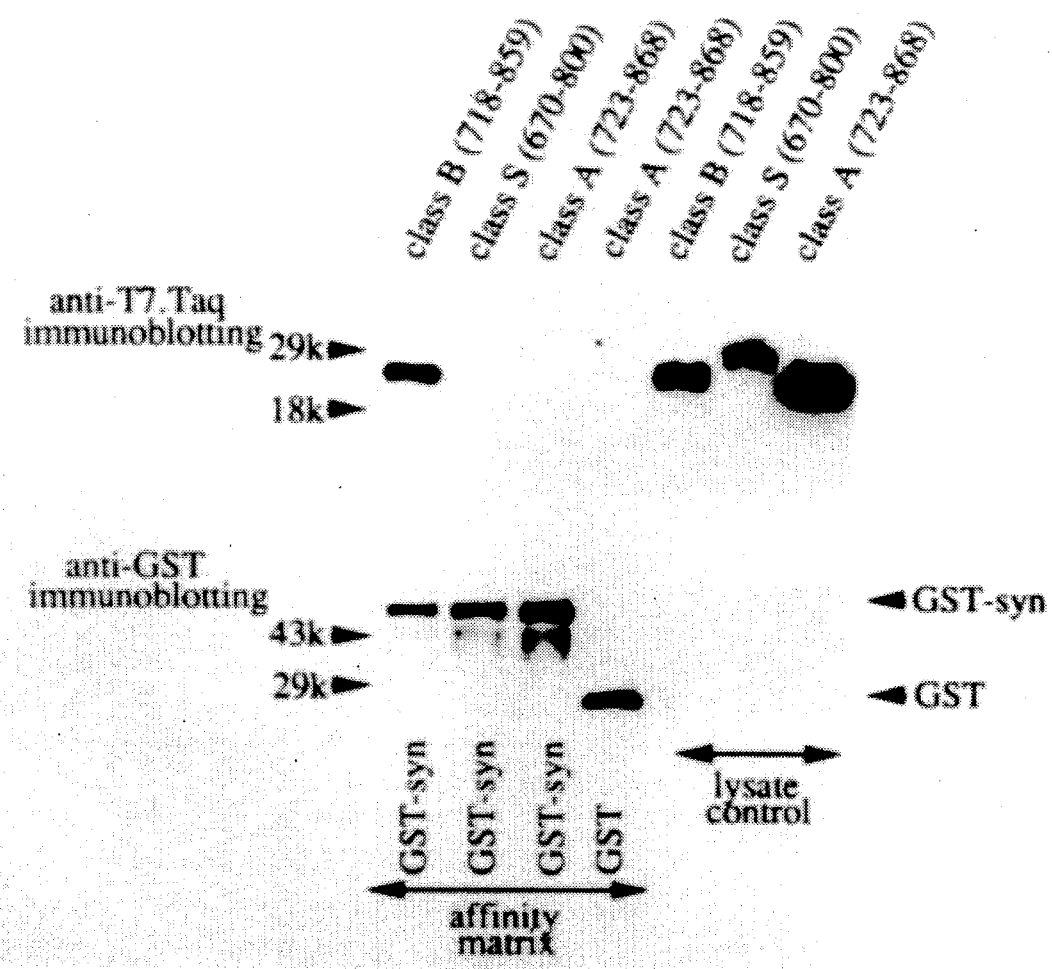
FIG. 8 is an immunoblot showing the interaction of the corresponding regions from $\alpha 1_A$ and $\alpha 1_S$ with syntaxin 1A. His-fusion proteins with the corresponding region (723–868) of the cytoplasmic loop $Ln._m$ of class A calcium channel and the entire $L_{II-III}$ loop (670–800) of L-type rabbit skeletal muscle calcium channel (class S) were expressed. The binding assays were performed as described for FIG. 2. Aliquots of lysates as indicated were incubated with GST-syntaxin (GST-syn) or GST-glutathione-Sepharose beads. Bound proteins were eluted and resolved by electrophoresis in SDS/PAGE and sequentially probed with anti-T7-Tag (top panel) and anti-GST (bottom panel) antibodies.
Figure 9:
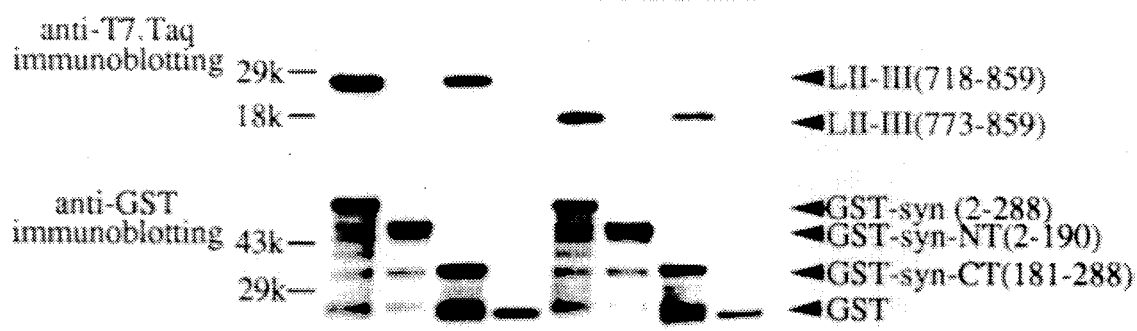
FIG. 9 is an immunoblot demonstrating the interaction of the amino and carboxyl terminal domains of syntaxin 1A with N-type calcium channels. Two GST-syntaxin fusion proteins containing the amino-terminal sequence, GST-syn-NT(2–190), and the carboxyl-terminal sequence, GST-syn-CT(181–288), were generated and used for affinity matrices. Approximately 2 µg of both His-fusion proteins, $L_{II-III}$ (718–859) and $L_{II-III}$ (773–859), containing the syntaxin-binding site, were loaded on affinity matrices with GST-syn, GST-syn-NT, GST-syn-CT, and GST. As indicated, bound His-fusion proteins were co-eluted with GST-fusion proteins and immunoblotted sequentially with anti-T7-Tag (top panel) and anti-GST (bottom panel) antibodies.

To test whether $\alpha 1_A$ shares a similar syntaxin binding activity to $\alpha 1_B$, His-fusion proteins containing the corresponding region (residues 723–868) of the cytoplasmic loop $L_{II-III}$ from $\alpha 1_A$ (Starr et al., Proc. Natl. Acad. Sci. USA 88:5621–5625, 1991) were constructed. As a control, a His-fusion protein covering the entire $L_{II-III}$ loop (residues 670–800) of the rabbit skeletal muscle L-type calcium channel ($\alpha 1_S$) (Tanabe et al., Nature 328:313–318, 1987) was included in parallel syntaxin-binding assays. As shown in FIG. 8, while the sequence (718–859) from $\alpha 1_B$ binds to GST-syntaxin, there is no detectable interaction between the corresponding region from $\alpha 1_A$ or $\alpha 1_S$ in the syntaxin-binding region. These results indicate that these weakly conserved regions of the cytoplasmic loop $L_{II-III}$ from class A and class S calcium channels do not bind to syntaxin.

Example 3

Partial Purification of Rat Class B N-Type Calcium Channels

Brain calcium channels were partially purified as previously described (Westenbroek et al., Neuron 9:1099–1115, 1992). Briefly, fifteen rat brains cortices from three-week-old Sprague-Dawley rats were homogenized in 130 ml of 320 mM sucrose, 5 mM TriS pH 7.4 and protease inhibitors (1 μg/ml each pepstain A, leupeptin, and aprotinin, 0.2 mM phenyl methanesulfonyl fluoride, and 0.1 mg/ml benzamidine) by 10 strikes with a glass-Teflon homogenizer. After a short centrifugation (5000 rpm, 2 minutes, SS34-rotor), the membranes contained in the supernatant were pelleted (42,000 rpm, 1 hour, in Ti45 rotor) and solubilized in 230 ml of 1.2% digitonin in PBS (150 mM NaCl, 300 mM KCl, and 10 mM sodium phosphate buffer (pH 7.4) for 15 rain on ice. Unsolubilized material was sedimented by centrifugation as before, and the supernatant was slowly poured over a 20 ml wheat germ agglutinin (WGA) Sepharose column (50 ml/hr.). The column was washed with 300 ml of 0.1% digitonin, 75 mM NaCl, 50 mM sodium phosphate, 10 mM Tris-HCl (pH 7.4) at a flow rate of 50 ml/hr.

Bound calcium channels were eluted with 100 mM N-acetyl-D-glucosamine in the same buffer at a flow rate of 50 ml/hr. Two ml fractions were collected, frozen and stored at −80° C. About 50% of the solubilized N-type calcium channels were specifically bound and eluted from WGA-Sepharose under these experimental conditions (Westenbroek et al., Neuron 9:1099–1115, 1992).

Example 4

Immunoprecipitation

The WGA extraction fraction was labeled for 2 hr on ice with 500 fmol [$^{125}$I]Tyr$^{22}$ω-CTx-GVIA (NEN-Dupont), diluted 10-fold with PBS, and incubated for 2 hr at 4° C. with either anti-CNB-1 antibody, which is directed against residues 851–867 of the $\alpha 1$ subunit of rat brain class B N-type calcium channel (Westenbroek et al., Neuron 9:1099–1115, 1992) or mAb 10H5, an anti-syntaxin antibody (Yoshida et al., J. Biol. Chem. 267:24925–24928, 1992). Immune complexes were recovered by the addition of 4 mg of protein A-Sepharose 4B swollen in TBS, rotation for 1 hour, and centrifugation. After three washes in PBS, immunoprecipitated radioactivity was counted.

Anti-CNB1 antibodies immunoprecipitated 85%±6% (n=3) of ω-CTx receptors were also immunoprecipitated by anti-syntaxin antibody mAb10H5, but not by control mouse IgG (1.6%±0.4%, n=3), indicating that only a small fraction of N-type channels remains associated with syntaxin after treatment with digitonin and subsequent WGA-Sepharose column purification. Thus, this procedure provides N-type calcium channels containing $\alpha 1B$ with only 12% of their syntaxin-binding sites occupied.

Example 5

Inhibition of Binding of [$^{125}$I]-ω-CTx-GVIA-Labeled N-Type Calcium Channels by the His-$L_{II-III}$ (773–859) Peptide Approximately 2 μg of either GST-syntaxin or GST were coupled to glutathione-Sepharose 4B beads in PBS/0.5% Triton X-100 for 1 hour at 4° C. After removal of unbound proteins by washing with PBS/0.1% Triton X-100 for three times, an equal amount of lysate containing either His-$L_{II-III}$ (773–859) or His-$L_{II-III}$ (1027–1145), as a non-inhibitor control, was added to the beads. After a 1 hr incubation, an equal amount of cpm of [$^{125}$I]-ω-CTx-GVIA-labeled N-type calcium channel was added to each reaction mixture. After a further 3 hour incubation, the beads were washed three times with PBS and the amount of bound receptor was assessed by direct counting.

As shown in FIG. 10B, GST-syntaxin bound 3276±191 cpm (n=3) of labeled N-type channels, whereas GST alone bound only 549±74 cpm (n=3). This observation shows directly that syntaxin can bind N-type calcium channels in vitro and strengthens the conclusion that N-type calcium channels are tightly associated with syntaxin Bennett et al., *Science* 257:255–259, 1992; Lévêque et al., *J. Biol. Chem.* 269:6306–6312, 1994; Yoshida et al., *J. Biol. Chem.* 267:24925–24928, 1992; O'Conner et al., *FEBS Lett.* 326:255–261, 1993). These results also confirm that GST-syntaxin fusion proteins attached to an affinity matrix maintain the binding activity for calcium channels.

In order to demonstrate that the binding sequence identified in in vitro binding assays represents the high affinity syntaxin-binding site in $\alpha 1_B$, the ability of the 87-amino-acid binding peptide to compete for binding of native N-type calcium channels to GST-syntaxin was analyzed. Peptide competition analysis demonstrated that the peptide, His-$L_{II-III}$ (773–859), specifically competed for the binding of N-type calcium channels to GST-syntaxin (FIG. 10C). In three independent experiments, a 78%±12% reduction in the specific binding of ω-CTx-labeled N-type calcium channels to GST-syntaxin in the presence of lysate containing peptide His-$L_{II-III}$ (773–859) was observed. Only a 10%±8% reduction was seen in the presence of a control lysate containing approximately the same amounts of the peptide His-$L_{II-III}$ (1027–1145), which contains the carboxyl terminus of $L_{II-III}$.

From the foregoing, it will be evident that, although specific embodiments of the invention have been described herein for purposes of illustration, various modifications may be made without deviating from the spirit and scope of the invention.

We claim:

1. A peptide consisting of the amino acid sequence of FIG. 11A from alanine, amino acid 773, to aspartic acid, amino acid 859.

2. A peptide consisting of the amino acid sequence of FIG. 11A from glutamic acid, amino acid 718, to aspartic acid, amino acid 859.

3. A peptide consisting of the amino acid sequence of FIG. 11A from glutamic acid, amino acid 718, to cysteine, amino acid 1141.

4. A peptide consisting of the amino acid sequence of FIG. 11A from an amino acid positioned between glutamic acid, amino acid 718, and alanine, amino acid 773, to an amino acid positioned between aspartic acid, amino acid 859, and cysteine, amino acid 1141.

5. A peptide consisting of an amino acid sequence of between 87 to 424 amino acid residues in length, wherein said amino acid sequence contains an amino acid sequence having at least 60% sequence similarity with the amino acid sequence of FIG. 11A from alanine, amino acid 773, to aspartic acid, amino acid 859.

6. A peptide consisting of the amino acid sequence of FIG. 11B from alanine, amino acid 772, to aspartic acid, amino acid 858.

7. A peptide consisting of the amino acid sequence of FIG. 11B from glutamic acid, amino acid 717, to aspartic acid, amino acid 858.

8. A peptide consisting of the amino acid sequence of FIG. 11B from glutamic acid, amino acid 717, to cysteine, amino acid 1143.

9. A peptide consisting of the amino acid sequence of FIG. 11B from an amino acid positioned between glutamic acid, amino acid 717, and alanine, amino acid 772, to an amino acid positioned between aspartic acid, amino acid 858, and cysteine, amino acid 1143.

10. A peptide consisting of an amino acid sequence of between 87 to 427 amino acid residues in length, wherein said amino acid sequence contains an amino acid sequence having at least 60% sequence similarity with the amino acid sequence of FIG. 11B from alanine, amino acid 772, to aspartic acid, amino acid 858.

11. A peptide consisting of the amino acid sequence of FIG. 12 from isoleucine, amino acid 181, to glycine, amino acid 288.

12. A method of screening for compounds that inhibit the interaction between presynaptic calcium channels and presynaptic vesicles, comprising the steps of:

(a) contacting a peptide according to any one of claims 1–10 with a candidate compound under conditions sufficient to permit binding between said peptide and said candidate compound; and (b) detecting the presence or absence of binding between said peptide and said candidate compound, thereby determining whether said candidate compound bound to said peptide.

13. A method of screening for compounds that inhibit the interaction between presynaptic calcium channels and presynaptic vesicles, comprising the steps of:

(a) incubating a candidate compound, a first peptide according to any one of claims 1–10, and a second peptide consisting of the amino acid sequence of FIG. 12 from isoleucine, amino acid 181, to glycine, amino acid 288, under conditions sufficient to permit binding between said first and second peptides; and (b) detecting the presence or absence of binding between said first and second peptides, thereby determining whether said candidate compound inhibited the binding.

14. A method of screening for compounds that inhibit the interaction between presynaptic calcium channels and presynaptic vesicles, comprising the steps of:

(a) incubating a first peptide according to any one of claims 1–10 and a candidate compound under conditions sufficient to permit binding between said peptide and said candidate compound, to form a reaction mixture;

(b) contacting a second peptide consisting of the amino acid sequence of FIG. 12 from isoleucine, amino acid 181, to glycine, amino acid 288, with said reaction mixture under conditions sufficient to permit binding between said first and second peptides; and (c) detecting the presence or absence of binding between said first and second peptides, thereby determining whether said candidate compound inhibited the binding.

15. A method of screening for compounds that inhibit the interaction between presynaptic calcium channels and presynaptic vesicles, comprising the steps of:

(a) incubating a candidate compound, a peptide according to any one of claims 1–10, and syntaxin under conditions sufficient to permit binding between said peptide and said syntaxin; and (b) detecting the presence or absence of binding between said peptide and said syntaxin, thereby determining whether said candidate compound inhibited the binding.

16. A method of screening for compounds that inhibit the interaction between presynaptic calcium channels and presynaptic vesicles, comprising the steps of:

(a) incubating a peptide according to any one of claims 1–10 and a candidate compound under conditions sufficient to permit binding between said peptide and said candidate compound, to form a reaction mixture;

(b) contacting syntaxin with said reaction mixture under conditions sufficient to permit binding between said peptide and said syntaxin; and (c) detecting the presence or absence of binding between said peptide and said syntaxin, thereby determining whether said candidate compound inhibited the binding.

* * * * *

UNITED STATES PATENT AND TRADEMARK OFFICE
CERTIFICATE OF CORRECTION

PATENT NO. : 5,623,051
DATED : April 22, 1997
INVENTOR(S) : William A. Catterall and Zu-Hang Sheng It is certified that error appears in the above-identified patent and that said Letters Patent is hereby corrected as shown below:

In column 1, line 5, before the "Technical Field" please insert the following:

--This invention was made with government support under grant number NS 22625 awarded by the National Institutes of Health. The government has certain rights in the invention.--

Signed and Sealed this

Twenty-fourth Day of March, 1998

Attest:

BRUCE LEHMAN

Attesting Officer     Commissioner of Patents and Trademarks